United States Patent
Doi et al.

(10) Patent No.: US 9,400,079 B2
(45) Date of Patent: Jul. 26, 2016

(54) AUTOMATIC BALANCING STRUCTURE OF MEDICAL BALANCING STAND

(71) Applicant: MITAKA KOHKI CO., LTD., Tokyo (JP)

(72) Inventors: Masao Doi, Tokyo (JP); Toshio Yamazaki, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 215 days.

(21) Appl. No.: 14/093,156

(22) Filed: Nov. 29, 2013

(65) Prior Publication Data

US 2014/0151522 A1 Jun. 5, 2014

(30) Foreign Application Priority Data

Nov. 30, 2012 (JP) .................................. 2012-262299

(51) Int. Cl.
*F16M 11/18* (2006.01)
*F16M 11/20* (2006.01)

(52) U.S. Cl.
CPC ........... *F16M 11/18* (2013.01); *F16M 11/2021* (2013.01); *A61B 2090/504* (2016.02); *F16M 2200/044* (2013.01)

(58) Field of Classification Search
CPC .............. F16M 11/18; F16M 11/2021; F16M 2200/044; A61B 19/5223; A61B 2019/264; B25J 19/0008; Y10S 901/27; Y10T 74/20305
USPC .............. 248/364, 162.1, 123.11, 404, 406.2, 248/410, 417, 418
See application file for complete search history.

(56) References Cited

U.S. PATENT DOCUMENTS

| 5,613,419 | A  | * | 3/1997  | Pierson  | B25J 19/0012 177/212 |
| 6,129,319 | A  | * | 10/2000 | Metelski | F16M 11/10 248/123.2 |
| 6,186,023 | B1 | * | 2/2001  | Nakamura | F16M 11/04 248/123.2 |
| 8,979,042 | B2 | * | 3/2015  | Doi      | F16M 11/2021 248/123.11 |
| 2013/0211651 | A1 | * | 8/2013 | Schaible | F16M 11/20 701/22 |

(Continued)

FOREIGN PATENT DOCUMENTS

| JP | 10-272143   | 10/1998 |
| JP | 2000-141251 | 5/2000  |
| JP | 2005-052679 | 3/2005  |

OTHER PUBLICATIONS

U.S. Appl. No. 14/095,467, to Masao Doi et al., which was filed Dec. 3, 2013.

(Continued)

*Primary Examiner* — Nkeisha Smith
(74) *Attorney, Agent, or Firm* — Greenblum & Bernstein, P.L.C.

(57) ABSTRACT

An automatic balancing structure of a medical balancing stand includes an elastic member arranged in each clearance C. In a normal state, a lever and a turn plate turn together through the elastic members, to follow a rotative movement of a lateral arm. When an imbalance occurs on the lateral arm, the lateral arm produces torque with which a contact part of the lever presses and deforms one of the elastic members to activate a corresponding one of switches S1 and S2. The activated switch outputs an imbalance detected signal to an adjustment unit, which resolves the imbalance. The switches S1 and S2 are simple to downsize the automatic balancing structure and are effective to carry out balance adjustment.

8 Claims, 7 Drawing Sheets

(56) References Cited

U.S. PATENT DOCUMENTS

2015/0083883 A1* 3/2015 Meuret ............... F16M 11/046
 248/542
2015/0226369 A1* 8/2015 Troy .................... F16M 11/18
 180/2.1

OTHER PUBLICATIONS

Office Action issued in Japan Patent Appl. No. JP 2012-262299, dated May 10, 2016, along with an English translation thereof.

* cited by examiner

AUTOMATIC BALANCING STRUCTURE OF MEDICAL BALANCING STAND

BACKGROUND OF THE INVENTION

1. Field of the Invention

The present invention relates to an automatic balancing structure of a medical balancing stand.

2. Description of Related Art

The medical balancing stand is used to support and suspend a medical device such as a surgical microscope at an optional position in midair. The medical balancing stand includes a vertical arm and a lateral arm. A first end of the lateral arm supports a relatively heavy load such as a surgical microscope and a second end of the lateral arm supports a counterweight to balance the load. An intermediate part of the lateral arm is provided with a turn shaft that is horizontally supported with the vertical arm so that the lateral arm is able to turn relative to the vertical arm.

The turn shaft has a clutch unit that is locked in a normal state to prevent the lateral arm from turning relative to the vertical arm. When moving the load (for example, a surgical microscope) supported at the first end of the lateral arm to an optional height position, an operator who may be a doctor releases the clutch unit and turns the surgical microscope together with the lateral arm. The lateral arm having the surgical microscope is balanced on the turn shaft due to the counterweight, and therefore, stops at an optional turned position in midair as if in a gravity-free state even if the operator removes his or her hands from the surgical microscope. Accordingly, the operator is able to freely change the position of the surgical microscope in midair. Once the position and orientation of the surgical microscope are optimized as required, the operator locks the clutch unit to fix the lateral arm at the position.

Balance of the lateral arm on the turn shaft is detected and adjusted with the use of an encoder that detects a turn angle of the turn shaft and a computer that adjusts the counterweight according to a signal from the encoder. In connection with this, a related art is disclosed in, for example, Japanese Unexamined Patent Application Publication No. 2005-52679.

SUMMARY OF THE INVENTION

The related art that employs the encoder and computer to balance the lateral arm is large and needs a complicated adjusting operation to deteriorate reliability. If the lateral arm is a multi-joint arm having a plurality of horizontal turn shafts, the related art must conduct further complicated operations because it must detect a turn angle of each turn shaft and balance the multi-joint arm according to the detected turn angles.

In consideration of the problems of the related art, the present invention provides an automatic balancing structure of a medical balancing stand, capable of independently establishing a balance on each horizontal turn shaft without using an encoder or a computer.

According to an aspect of the present invention, the medical balancing stand includes a first arm and a second arm, the second arm having a turn shaft which is horizontally fitted into a predetermined position of the first arm and with which the second arm is turnable relative to the first arm, a first end of the second arm supporting a load, a second end of the second arm having an adjustment unit to balance the second arm on the turn shaft. The automatic balancing structure of the medical balancing stand includes a lever that is attached to the turn shaft, is fixed relative to the second arm, and has a contact part at a front end thereof, a turn plate that is attached to the turn shaft so as to freely turn around the turn shaft and has a pair of stoppers that are arranged on each side of the contact part with a predetermined clearance from the contact part, a contact detector that is arranged on the pair of stoppers and outputs, according to a contact state with the contact part, a balance information signal to the adjustment unit, a clutch unit that is fixed to the first arm and engages with a part of the turn plate to lock the turn plate, and an elastic member that is arranged in each of the clearances and is deformed when receiving pressure caused by an imbalance occurring on the second arm. In a normal state, the turn plate turns with the lever through the elastic members. In a balance adjusting state, the clutch unit locks the turn plate and the contact part deforms the elastic member to activate the contact detector so that the contact detector outputs the balance information signal to the adjustment unit to balance the second arm.

DESCRIPTION OF PREFERRED EMBODIMENTS

An automatic balancing structure of a medial balancing stand according to an embodiment of the present invention will be explained with reference to the drawings.

Figure 1:
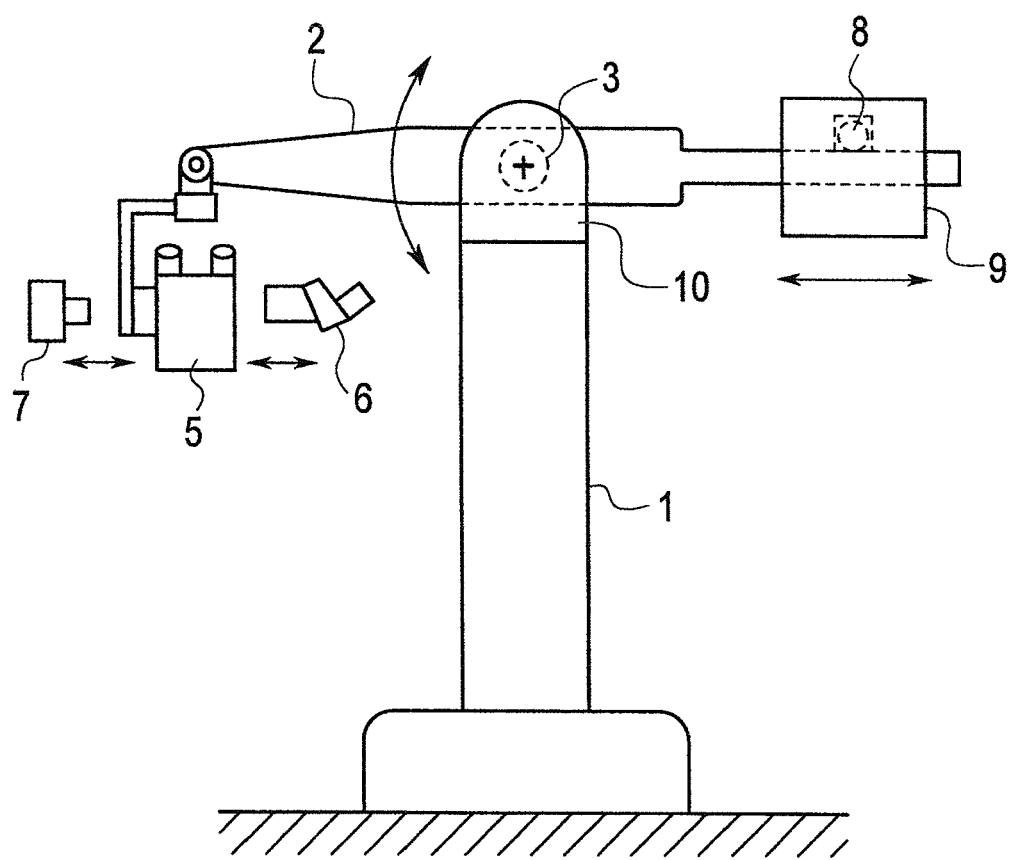
FIG. 1 is a side view illustrating a medical balancing stand employing an automatic balancing structure according to an embodiment of the present invention.
Figure 2:
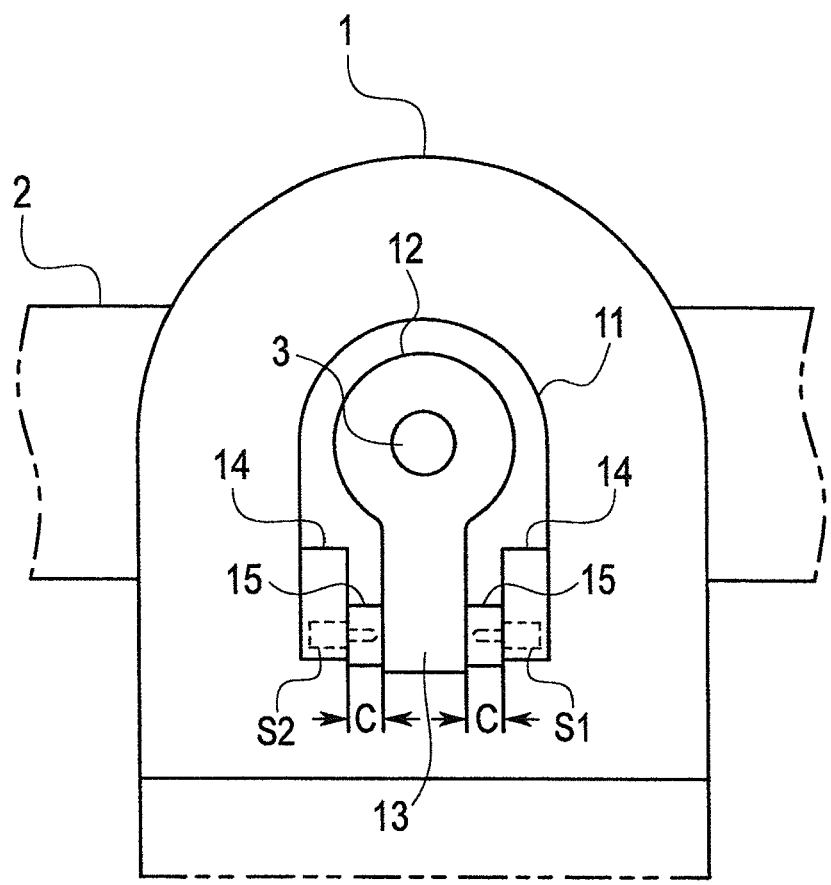
FIGS. 2, 3, and 4 are front, perspective, and partly sectioned front views illustrating a lever and turn plate of the automatic balancing structure.
Figure 3:
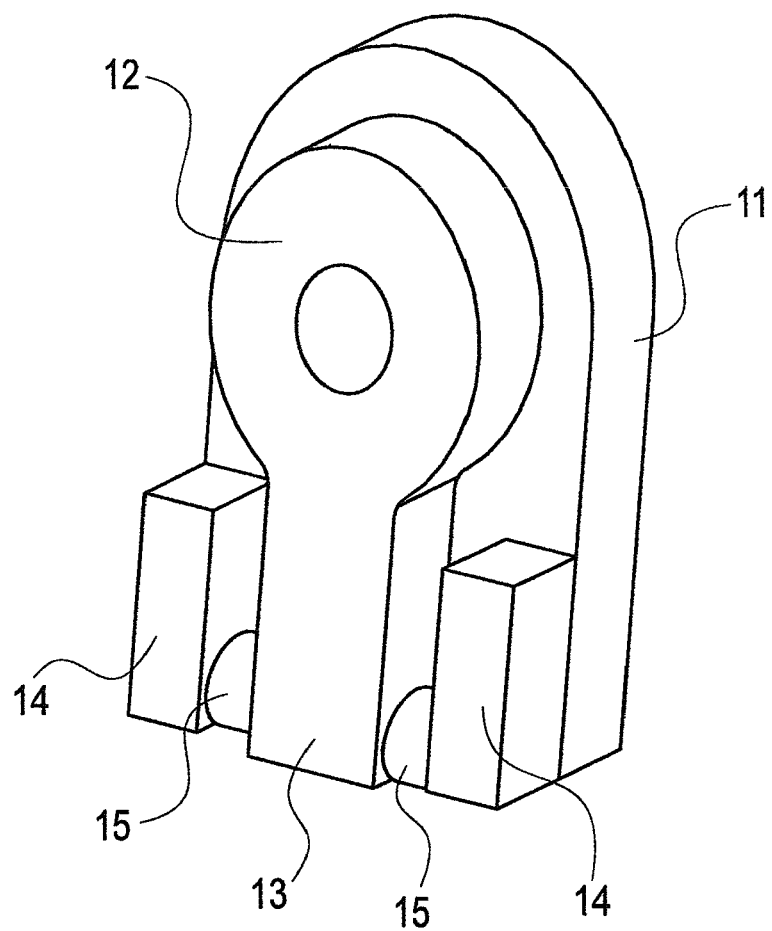
Figure 4:
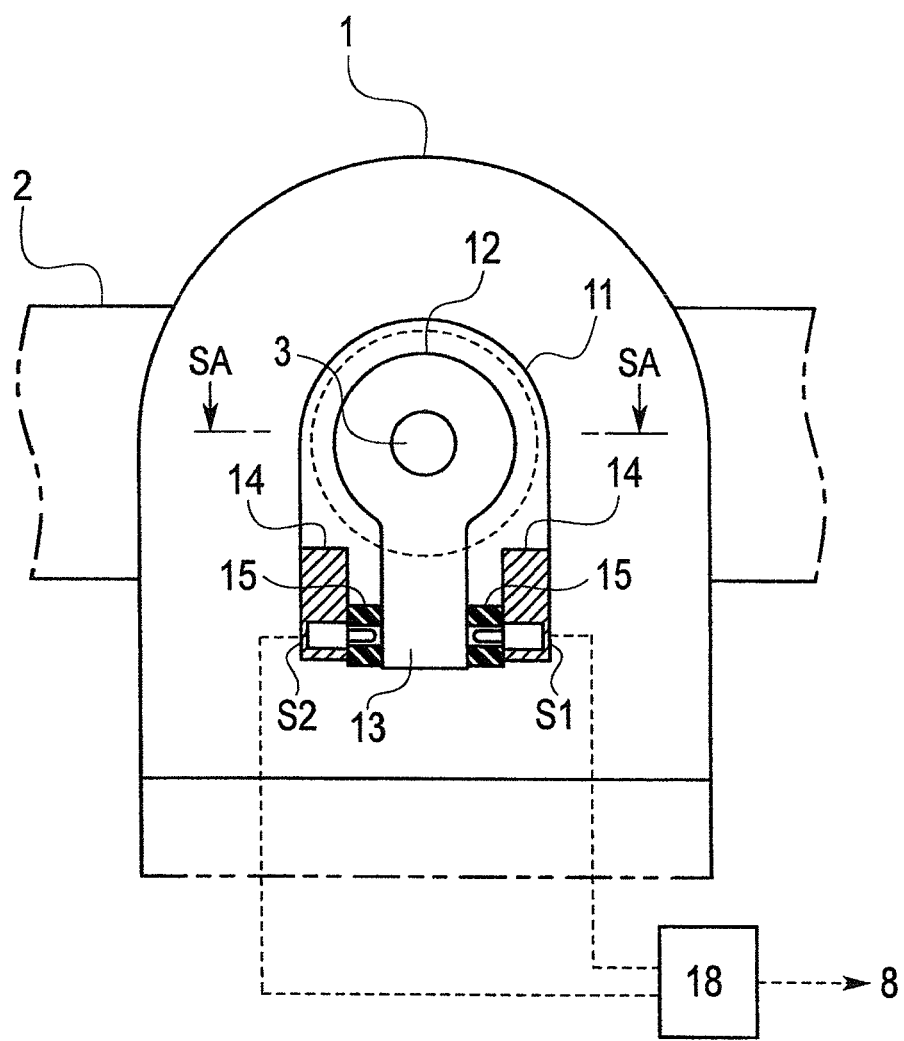

In FIG. 1, the medical balancing stand includes a vertical arm 1 (corresponding to the "first arm" in the claims) that is fixed relative to, for example, a floor that has a predetermined positional relationship with respect to a gravitational direction. An upper end of the vertical arm 1 rotatably supports an intermediate part of a lateral arm 2 (corresponding to the "second arm" in the claims). The lateral arm 2 integrally has a turn shaft 3 that horizontally passes through the upper part of the vertical arm 1 and is supported with a bearing 4. Namely, a main axis of the turn shaft 3 is horizontally fixed with respect to the vertical arm 1 and the lateral arm 2 is turnable around the main axis of the turn shaft 3.

A first end of the lateral arm 2 supports a relatively heavy load such as a surgical microscope 5, a side microscope 6, and a camera 7. The side microscope 6 and camera 7 are detachably attached to the surgical microscope 5. When these items are detached from the surgical microscope 5, the weight of the load changes.

A second end of the lateral arm 2 has a counterweight 9 that is moved by a motor 8. The motor 8 and counterweight 9 form the "adjustment unit" stipulated in the claims.

Figure 5:
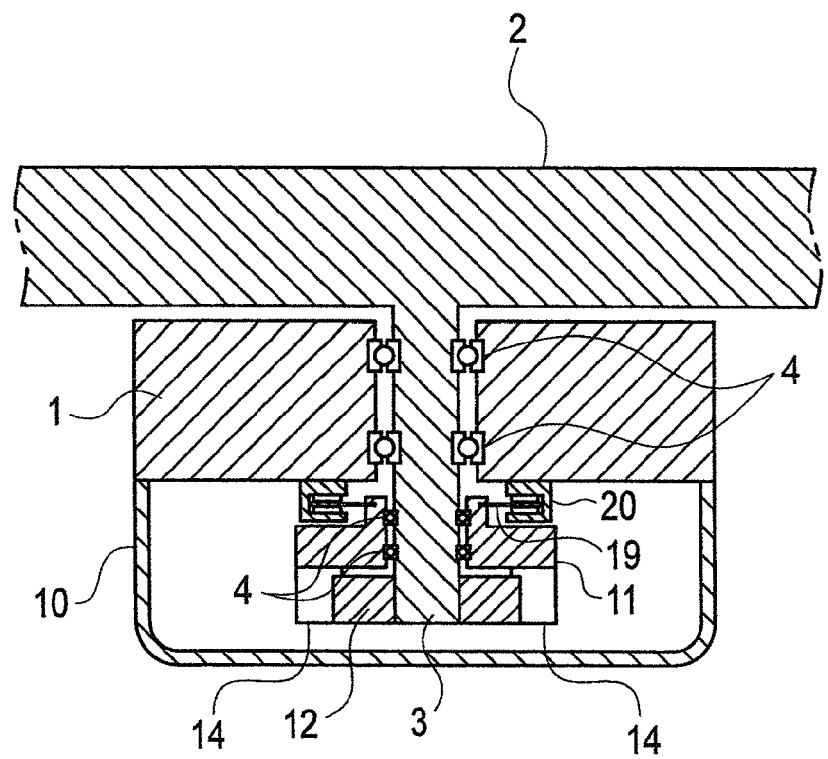
FIG. 5 is a sectional view along a line SA-SA of FIG. 4.
Figure 6:
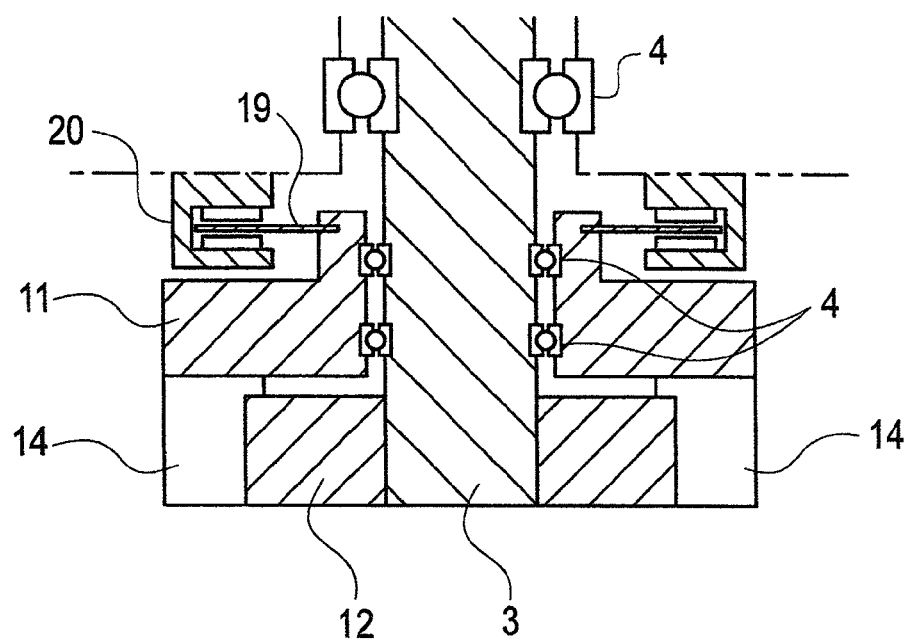
FIG. 6 is an enlarged sectional view illustrating part of the lever and turn plate of FIG. 5.
Figure 7:
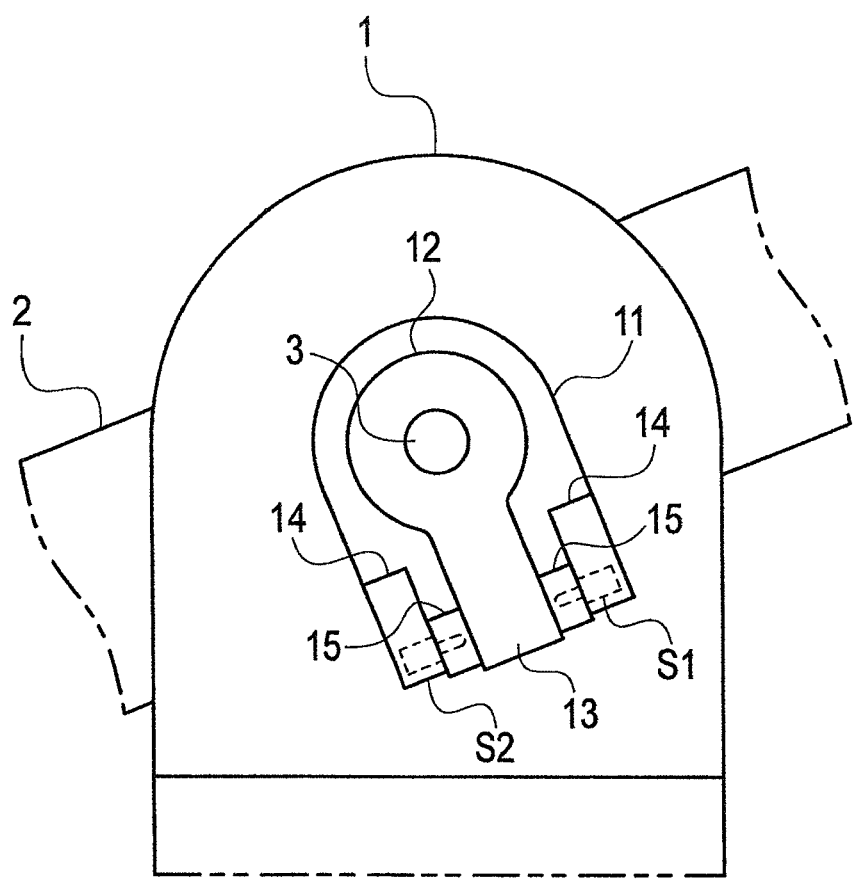
FIG. 7 is a front view illustrating the lever, turn plate, and lateral arm turned together from the state of FIG. 2.

The upper end of the vertical arm 1 where the turn shaft 3 of the lateral arm 2 horizontally passes through is covered with a cover 10 (FIG. 5). Inside the cover 10, a turn plate 11 is supported with a bearing 4 so that the turn plate 11 is turnable relative to the turn shaft 3.

A front end of the turn shaft 3 is passed through the turn plate 11 and is fixed to a lever 12 that turns together with the turn shaft 3. Namely, the lever 12 is fixed through the turn shaft 3 relative to the lateral arm 2, and therefore, a position (angle) of the lever 12 reflects a position of the lateral arm 2.

The lever 12 integrally has a contact part 13 that downwardly extends when the lateral arm 2 is horizontal. On each side of the contact part 13, the turn plate 11 has a stopper 14 that is spaced away from the contact part 13 by a clearance C.

Each stopper 14 has an elastic member 15 whose width corresponds to the clearance C. The elastic member 15 is cylindrical and is made of hard rubber. Although the turn plate 11 is not fixed to the vertical arm 1 nor to the lateral arm 2, a movement of the turn plate 11 around the turn shaft 3 is restricted when the elastic member 15 of any one of the stoppers 14 of the turn plate 11 comes in contact with the contact part 13 of the lever 12.

The stoppers 14 are provided with switches S1 and S2, respectively. The switches S1 and S2 as a contact detector each has a sensing part such as a push button protruding into a hollow of the elastic member 15 to detect deformation of the elastic member 15. When a moving amount of the sensing part exceeds a predetermined value, the switch S1 (S2) turns on or off to output a contact signal indicating that the switch is in contact with the contact part 13 of the lever 12. The contact signal serves as a balance information signal that indicates one of three states, i.e., a first imbalanced state in which the switch S1 provides the contact signal, a second imbalanced state in which the switch S2 provides the contact signal, and a balanced state in which none of the switches S1 and S2 provides the contact signal. The balance information signal is supplied to a controller 18. According to the signal, the controller 18 feedback-controls the motor 8 to move the counterweight 9 and restore a balanced state.

The back of the turn plate 11 is provided with a circular flange 19 around the turn shaft 3. The vertical arm 1 is fixedly provided with a clutch 20. When instructed, the clutch 20 holds and locks the flange 19 so that the turn plate 11 becomes substantially immovable around the turn shaft 3. The flange 19 and clutch 20 form the "clutch unit" stipulated in the claims.

Operation of the automatic balancing structure according to the embodiment will be explained.

When the clutch 20 is released, the turn plate 11 is turnable. In this state, the turn plate 11 and lever 12 turn together due to the presence of the elastic members 15 in the clearances C, to follow a movement of the turn shaft 3 of the lateral arm 2. When the turn plate 11 is freely turnable, the elastic members 15 cause no deformation, and therefore, the switches S1 and S2 are not operative.

When a doctor or an operator who manipulates the surgical microscope 5 wants to change a vertical position of the surgical microscope 5, the doctor turns the lateral arm 2. To achieve this, the doctor pushes a button (not illustrated) on the surgical microscope 5 to release the clutch 20 and turns the lateral arm 2 by holding and moving the surgical microscope 5. Since the surgical microscope 5 is balanced with the counterweight 9, the doctor can easily and lightly turn the lateral arm 2.

At a required position, the doctor removes his or her hands from the surgical microscope 5, which stops at the position because the lateral arm 2 having the surgical microscope 5 is balanced. When the doctor releases his or her finger from the button (not illustrated) on the surgical microscope 5, the clutch 20 locks the flange 19 of the turn plate 11 to fix the lateral arm 2 at the position.

When the clutch 20 is locked, the lateral arm 2 is almost unable to turn due to the presence of the elastic members 15 between the lever 12 and the turn plate 11.

If the side microscope 6 or the camera 7 is attached to or detached from the surgical microscope 5, the balanced state breaks into an imbalanced state that must be corrected.

Figure 8:
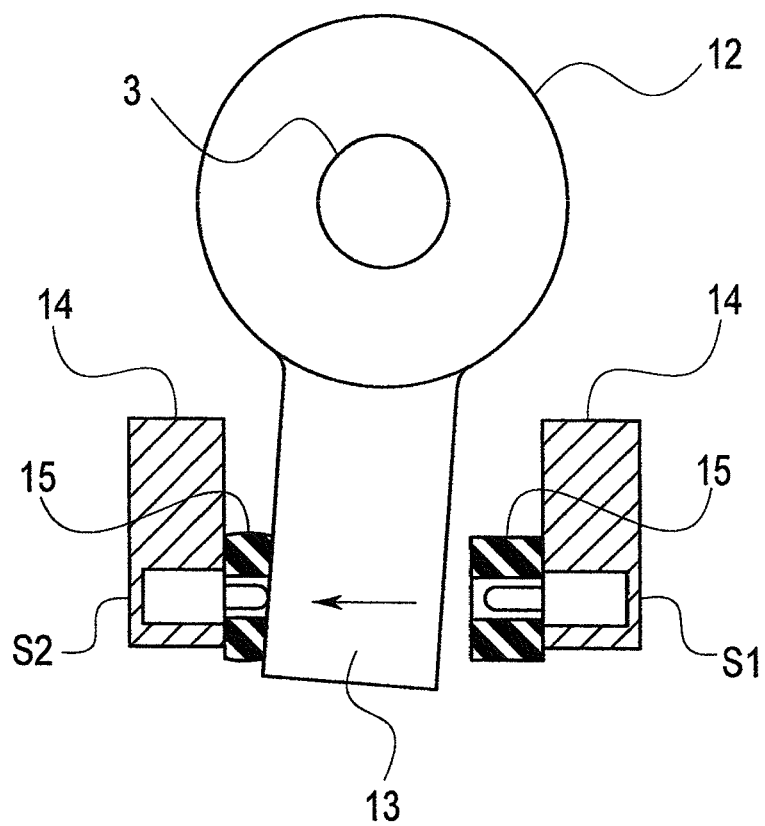
FIG. 8 is a sectional view illustrating a contact part of the lever in a turned state, an elastic member deformed by the contact part, and a switch in contact with the contact part.

To attach or detach, for example, the camera 7, the clutch 20 is first locked. When the camera 7 is attached to or detached from the surgical microscope 5, the balance of the lateral arm 2 on the turn shaft 3 breaks to cause torque to turn the lateral arm 2. Together with the lateral arm 2, the lever 12 fixed to the turn shaft 3 of the lateral arm 2 turns so that the contact part 13 of the lever 12 presses and deforms one of the resilient members 15 as illustrated in FIG. 8. As a result, the contact part 13 comes in contact with the switch (S2 in FIG. 8) to activate the switch.

The activated switch S2 outputs a signal indicating the second imbalanced state to the controller 18. In response to the signal, the controller 18 outputs a feedback signal to the motor 8 to move the counterweight 9 in a direction to correct the imbalanced state. When the imbalanced state is corrected to a balanced state, the contact part 13 of the lever 12 moves away from the switch S2, and therefore, the contact detector (the switches S1 and S2) outputs a signal indicating the balanced state to the controller 18. Then, the controller 18 stops the motor 8 to keep the counterweight 9 at the position so that the lateral arm 2 is kept balanced on the turn shaft 3. If any one of the first and second imbalanced states occurs even slightly, torque occurs around the turn shaft 3 to turn the lateral arm 2, and therefore, the imbalanced state is instantaneously and surely detected by the contact detector (the switches S1 and S2).

After the camera 7 or the like is attached to or detached from the surgical microscope 5 and the balanced state is reestablished, the resilient member 15 deformed between the contact part 13 of the lever 12 and the stopper 14 of the turn plate 11 restores an undeformed original shape. Then, the clutch 20 may be released to adjust the vertical position of the surgical microscope 5 to or from which the camera 7 or the like has been attached or detached.

In this way, the embodiment employs no encoder or computer. Only with the switches S1 and S2, the embodiment detects one of the three states, i.e., the first and second imbalanced states and balanced state, and according to the detected state, adjusts the balance of the lateral arm 2 on the turn shaft 3. Accordingly, the embodiment is capable of downsizing the medical balancing stand. The balancing operation according to the embodiment is easy to carry out at high speed and is stable and reliable.

If the lateral arm 2 is a multi-joint arm having a plurality of horizontal turn shafts, the embodiment is capable of independently achieving the balancing operation on each of the turn shafts and thereby totally balancing the multi-joint arm.

Although the elastic member 15 is attached to the stopper 14 of the turn plate 11 according to the embodiment, the elastic member 15 may be attached to both the contact part 13 and stopper 14 if the switch S1 (S2) is configured to operate in response to even a fine deformation of the elastic member 15.

Although the contact detector employs the two switches S1 and S2 according to the embodiment, only one switch will be sufficient in a case where the switch is able to detect a turn direction of the lever 12.

In this way, the present invention employs no encoder or computer. Instead, the present invention employs ON/OFF switches to easily establish a balanced state and downsize the automatic balancing structure of the medical balancing stand.

Even if the medical balancing stand employs a multi-joint lateral arm having a plurality of horizontal turn shafts, the present invention is able to separately adjust the turn shafts to balance the multi-joint lateral arm on the turn shafts.

According to the present invention, the resilient members exist in the clearances, and therefore, the lever and turn plate turn together to follow a movement of the second arm without bothering the movement of the second arm. In a balanced state, the second arm having the turn shaft turns with light force relative to the first arm, and when an operator removes his or her hands from the second arm, stops at the position. The stopped state of the second arm may be locked with the clutch unit. In the locked state, the elastic members prevent the second arm from largely playing relative to the first arm, and in this state, the medical balancing stand can safely be moved for storage or transportation.

If the second arm is put into an imbalanced state, the clutch unit is used to lock the turn plate. This creates torque and pressure to deform one of the elastic members and the contact part of the lever comes in contact with the switch corresponding to the deformed elastic member.

Then, the switch outputs a signal indicating the imbalanced state to the adjustment unit, which acts to solve the imbalanced state and restore the balanced state.

The adjustment unit according to the present invention employs the movable counterweight that is able to simplify the adjustment unit.

According to the present invention, the contact detector outputs a signal indicating one of the three states, i.e., the first and second imbalanced states and balanced state to the adjustment unit. The only three kinds of signals make the control of the adjustment unit simpler, more stable, and more reliable.

To control the adjustment unit, the present invention employs the contact detector that includes only a pair of switches. With this compact control system, the present invention is capable of feedback-controlling the adjustment unit at high speed.

This patent application claims the benefit of priority under 35 U.S.C. 119(a) to Japanese Patent Application No. 2012-262299 filed on Nov. 30, 2012 whose disclosed contents are incorporated by reference herein.

What is claimed is:

1. An automatic balancing structure of a medical balancing stand, the medical balancing stand having a first arm and a second arm, the second arm being turnable about a turn shaft that is horizontally fixed relative to the first arm, a first end of the second arm supporting a load, a second end of the second arm having an adjustment unit to balance the second arm on the turn shaft, the automatic balancing structure comprising:
    a lever fixed through the turn shaft relative to the second arm and having a contact part at a front end thereof;
    a turn plate rotatably fixed to the turn shaft and having a pair of stoppers arranged on each side of the contact part with a predetermined clearance from the contact part;
    a contact detector arranged within each of the stoppers and configured to output a balance information signal to the adjustment unit according to a contact state with the contact part;
    a clutch unit that is fixed to the first arm and engages with a part of the turn plate to lock the turn plate; and
    an elastic member arranged between one the stoppers and the contact part, and another elastic member arranged between other one of the stoppers and the contact part, each of the elastic members having an elasticity to be deformed when receiving pressure caused by an imbalance occurring on the second arm, wherein
    in a normal state, the turn plate turns with the lever through the elastic members, and
    in a balance adjusting state, the clutch unit locks the turn plate and the contact part deforms one of the elastic members to activate one of the contact detectors so that the activated contact detector outputs the balance information signal to the adjustment unit and the adjustment unit balances the second arm according to the balance information signal.

2. The automatic balancing structure of the medical balancing stand of claim 1, wherein
    the adjustment unit includes a counterweight that is arranged at the second end of the second arm and is moved according to the balance information signal for balancing the second arm.

3. The automatic balancing structure of the medical balancing stand of claim 1, wherein
    the activated contact detector detects one of a state that the contact part is closer to one of the stoppers, a state that the contact part is closer to the other one of the stoppers, and a state that the contact part is closer to none of the pair of stoppers, and outputs the balance information signal according to the detected state.

4. The automatic balancing structure of the medical balancing stand of claim 3, wherein
    each of the contact detectors includes a switch.

5. The automatic balancing structure of the medical balancing stand of claim 4, wherein
    a sensing part included in each one of the switches is configured to protrude through a hollow area of each of the elastic members for detecting deformation of the elastic members.

6. The automatic balancing structure of the medical balancing stand of claim 1, wherein
    the elastic members are in contact with the contact part without deformation when the second arm is in balance.

7. The automatic balancing structure of the medical balancing stand of claim 1, wherein
    the elastic member deformed in the balance adjusting state and the activated contact detector are disposed on a same side with respect to the contact part.

8. The automatic balancing structure of the medical balancing stand of claim 1, wherein
    the stoppers rotate in parallel with the turn plate.

* * * * *